United States Patent
Fenton

(10) Patent No.: US 10,973,676 B2
(45) Date of Patent: *Apr. 13, 2021

(54) MOUNTING ASSEMBLIES FOR OSTOMY APPLIANCES COMPRISING AN ADHESIVE SKIN BARRIER MEMBER HAVING A MULTI-PETALED OUTER PERIMETER

(71) Applicant: Marlen Manufacturing and Development Co., Bedford, OH (US)

(72) Inventor: Gary H. Fenton, Pepper Pike, OH (US)

(73) Assignee: MARLEN MANUFACTURING AND DEVELOPMENT CO., Bedford, OH (US)

( * ) Notice: Subject to any disclaimer, the term of this patent is extended or adjusted under 35 U.S.C. 154(b) by 695 days.

This patent is subject to a terminal disclaimer.

(21) Appl. No.: 15/548,294

(22) PCT Filed: Dec. 9, 2016

(86) PCT No.: PCT/US2016/065787
§ 371 (c)(1),
(2) Date: Aug. 2, 2017

(87) PCT Pub. No.: WO2017/087993
PCT Pub. Date: May 26, 2017

(65) Prior Publication Data
US 2018/0021164 A1    Jan. 25, 2018

Related U.S. Application Data

(60) Provisional application No. 62/335,208, filed on May 12, 2016.

(51) Int. Cl.
*A61F 5/443* (2006.01)
*A61F 5/448* (2006.01)
(Continued)

(52) U.S. Cl.
CPC .............. *A61F 5/443* (2013.01); *A61F 5/445* (2013.01); *A61F 5/448* (2013.01); *A61F 13/02* (2013.01);
(Continued)

(58) Field of Classification Search
CPC combination set(s) only.
See application file for complete search history.

(56) References Cited

U.S. PATENT DOCUMENTS

D201,737 S    7/1965  Ilg
3,690,320 A   9/1972  Riely et al.
(Continued)

FOREIGN PATENT DOCUMENTS

EP    0272816 A2    6/1988
EP    0882437 A2    12/1998
(Continued)

OTHER PUBLICATIONS

International Search Report and Written Opinion issued in corresponding PCT application No. PCT/US2016/065787 dated Feb. 17, 2017, 7 pages.
(Continued)

*Primary Examiner* — Guy K Townsend
(74) *Attorney, Agent, or Firm* — Pearne & Gordon LLP

(57) ABSTRACT

A mounting assembly for an ostomy appliance is disclosed. The mounting assembly comprises a body flange comprising a flexible plastic member comprising a flange ring, a rim, and first and second loops, and an adhesive skin barrier member. The mounting assembly also comprises an ostomy pouch comprising a proximal sheet having an aperture, a distal sheet, and a pouch ring attached to the proximal sheet, surrounding the aperture, the pouch ring comprising an adhesive coating thereon and third and fourth loops extending radially therefrom. The body flange and ostomy pouch
(Continued)

are configured for the third and fourth loops to engage within the pocket of the first and second loops, respectively, the pouch ring to fit around the flange ring, and the rim of the flexible plastic member to contact the adhesive coating on the pouch ring. The adhesive skin barrier member has a multi-petaled outer perimeter.

12 Claims, 7 Drawing Sheets

(51) Int. Cl.
    *A61F 13/02* (2006.01)
    *A61F 5/445* (2006.01)
    *A61F 13/00* (2006.01)

(52) U.S. Cl.
    CPC ............ *A61F 2005/4483* (2013.01); *A61F 2013/00978* (2013.01)

(56) References Cited

U.S. PATENT DOCUMENTS

| | | | |
|---|---|---|---|
| D257,063 S | 9/1980 | Galindo | |
| 4,592,750 A | 6/1986 | Kay | |
| 4,762,738 A | 8/1988 | Keyes et al. | |
| D303,574 S | 9/1989 | Steer | |
| D303,575 S | 9/1989 | Steer | |
| 4,988,343 A | 1/1991 | Ballan | |
| 5,207,652 A * | 5/1993 | Kay | A61M 25/02 |
| | | | 128/DIG. 26 |
| D354,560 S | 1/1995 | Chase | |
| D379,654 S | 6/1997 | Holtermann | |
| D398,990 S | 9/1998 | Briggs et al. | |
| D398,991 S | 9/1998 | Briggs et al. | |
| D460,550 S | 7/2002 | Falconer | |
| 6,508,794 B1 | 1/2003 | Palumbo et al. | |
| 6,589,221 B1 | 7/2003 | Olsen et al. | |
| D487,313 S | 3/2004 | Mazzella | |
| D496,727 S | 9/2004 | Kubalak | |
| 6,790,200 B2 * | 9/2004 | Fenton | A61F 5/445 |
| | | | 604/332 |
| 6,802,831 B2 | 10/2004 | Plass et al. | |
| 6,916,312 B2 | 7/2005 | Kondo et al. | |
| 7,049,478 B1 * | 5/2006 | Smith | A61F 13/067 |
| | | | 128/892 |
| 7,101,357 B2 | 9/2006 | Tanaka et al. | |
| D533,273 S | 12/2006 | Witt | |
| 7,223,260 B2 | 5/2007 | Hansen et al. | |
| D552,237 S | 10/2007 | Needham et al. | |
| 7,586,019 B2 * | 9/2009 | Oelund | A61F 5/443 |
| | | | 128/888 |
| D607,559 S | 1/2010 | Schena | |
| D618,791 S | 6/2010 | Schena | |
| 8,328,779 B2 | 12/2012 | Fenton | |
| 8,399,732 B2 | 3/2013 | Oelund et al. | |
| 8,409,157 B2 * | 4/2013 | Haggstrom | A61F 13/0209 |
| | | | 604/315 |
| 8,409,158 B2 * | 4/2013 | Edvardsen | A61F 5/443 |
| | | | 604/318 |
| D683,451 S | 5/2013 | Todd et al. | |
| D691,730 S | 10/2013 | Smith et al. | |
| 8,672,908 B2 | 3/2014 | Todd et al. | |
| D737,453 S | 8/2015 | Gergely et al. | |
| D744,090 S | 11/2015 | Bendix et al. | |
| D753,820 S | 4/2016 | Lohse | |
| D766,448 S | 9/2016 | Gergely et al. | |
| D768,294 S | 10/2016 | Brezoczky | |
| D778,435 S | 2/2017 | Grogan | |
| D785,189 S | 4/2017 | Dettmar | |
| 9,622,903 B2 * | 4/2017 | Israelson | A61F 5/448 |
| 10,470,918 B2 * | 11/2019 | Bendix | A61F 5/445 |
| 10,517,754 B2 * | 12/2019 | Praame | A61F 5/443 |
| 2002/0032418 A1 | 3/2002 | Iseke | |
| 2002/0032428 A1 * | 3/2002 | Lindstrom | A61F 13/64 |
| | | | 604/392 |
| 2002/0088080 A1 | 7/2002 | Fenton | |
| 2003/0100920 A1 | 5/2003 | Akin et al. | |
| 2003/0236509 A1 | 12/2003 | Silvestrini | |
| 2004/0106908 A1 * | 6/2004 | Leise, Jr. | A61F 5/448 |
| | | | 604/332 |
| 2006/0195053 A1 * | 8/2006 | Oelund | A61F 5/448 |
| | | | 602/43 |
| 2006/0276763 A1 | 12/2006 | Keyes | |
| 2011/0218507 A1 * | 9/2011 | Andersen | A61F 5/445 |
| | | | 604/338 |
| 2012/0143154 A1 * | 6/2012 | Edvardsen | A61F 5/4404 |
| | | | 604/318 |
| 2012/0143155 A1 * | 6/2012 | Edvardsen | A61F 5/443 |
| | | | 604/318 |
| 2014/0114265 A1 * | 4/2014 | Israelson | A61F 5/443 |
| | | | 604/342 |
| 2017/0143535 A1 * | 5/2017 | Praame | A61F 5/445 |
| 2017/0224523 A1 * | 8/2017 | Bendix | A61F 5/443 |
| 2018/0021164 A1 * | 1/2018 | Fenton | A61F 5/445 |
| | | | 604/336 |
| 2018/0021165 A1 * | 1/2018 | Fenton | A61F 5/445 |
| | | | 604/338 |
| 2018/0104089 A1 * | 4/2018 | Nyberg | A61F 5/443 |
| 2018/0235801 A1 * | 8/2018 | Oellgaard | A61F 5/445 |
| 2019/0133812 A1 * | 5/2019 | Seres | A61F 5/445 |

FOREIGN PATENT DOCUMENTS

| | | | | |
|---|---|---|---|---|
| GB | 2311467 A | | 10/1997 | |
| JP | S63181758 A | | 7/1988 | |
| JP | H10248867 A | | 9/1998 | |
| JP | 1036292 | | 4/1999 | |
| JP | 1036293 | | 4/1999 | |
| JP | 2005514075 A | | 5/2005 | |
| JP | 2011521725 A | | 7/2011 | |
| WO | 2015180731 A1 | | 12/2015 | |
| WO | WO-2015180731 A1 * | | 12/2015 | A61F 5/443 |
| WO | 2016151303 A1 | | 9/2016 | |
| WO | 2017075634 A1 | | 5/2017 | |

OTHER PUBLICATIONS

"A New Vision in Patient Care Introducing Kwick-View from Marlen", Product Literature, Accessed: May 11, 2016, 1 Page, Marlen Manufacturing & Development Company, Bedford, Ohio, USA.

"MARLEN UltraLite One-Piece Disposable, Drainable System for Ileostomies and Colostomies", Product Literature, © 2006, 2 Pages, Marlen Mfg. & Dev. Co., Bedford, Ohio, USA.

"Marlen UltraMax One-Piece Disposable Ostomy System", Product Literature, © 2005, 3 Pages, Marlen Manufacturing & Development Company, Bedford, Ohio, USA.

"UltraMax Gemini 2-Piece Disposal Adhesive Ostomy System", Product Literature, © 2008, 3 Pages, Marlen Manufacturing & Development Company, Bedford, Ohio, USA.

"Ultra-Moldable, Ultra-Flexible UltraSeal Flexible Barrier Ring", Product Literature, © 2006, 1 Page, Marlen Manufacturing & Development Company, Bedford, Ohio, USA.

Applicant's Design U.S. Appl. No. 29/564,314, filed May 12, 2016; Inventor: Gary H. Fenton; Applicant and Assignee: Marlen Manufacturing and Development Co; Filing receipt, specification and drawings provided herewith.

Search Report for European Application No. 16867368.9 dated Dec. 13, 2019, 9 pages.

Notice of Reasons for Rejection for Japanese Patent Application No. 2018-559892 dated Nov. 26, 2019, 10 pages (English translation included).

Canadian Examination for Application No. 3,023,435 dated Jan. 2, 2020, 5 pages.

(56) References Cited

OTHER PUBLICATIONS

Search Report for European Application No. 16867368.9 dated Aug. 10, 2020, 7 pages.

\* cited by examiner

A  B

A  B

MOUNTING ASSEMBLIES FOR OSTOMY APPLIANCES COMPRISING AN ADHESIVE SKIN BARRIER MEMBER HAVING A MULTI-PETALED OUTER PERIMETER

FIELD OF THE INVENTION

The present invention relates generally to mounting assemblies for ostomy appliances, and more particularly to mounting assemblies for ostomy appliances comprising (a) a body flange comprising (i) a flexible plastic member comprising a flange ring projecting axially from the body flange, a rim, and first and second loops extending radially from the rim, each of the first and second loops comprising a raised fence around an opening that forms a pocket, and (ii) an adhesive skin barrier member located on an opposite second side of the body flange, and (b) an ostomy pouch comprising (i) a proximal sheet having an aperture, (ii) a distal sheet, and (iii) a pouch ring attached to the proximal sheet, surrounding the aperture, the pouch ring comprising an adhesive coating on the pouch ring and third and fourth loops extending radially from the pouch ring, wherein the body flange and ostomy pouch are configured for the third and fourth loops to engage within the pocket of the first and second loops, respectively, the pouch ring to fit around the flange ring, and the rim of the flexible plastic member to contact the adhesive coating on the pouch ring, and further wherein the adhesive skin barrier member has a multi-petaled outer perimeter that has a shape corresponding to 2 to 8 petals extending radially from the adhesive skin barrier member, distributed uniformly around the adhesive skin barrier member, and separated by notches that expand radially from the adhesive skin barrier member.

BACKGROUND OF THE INVENTION

Ostomates are individuals that have undergone a surgery to create an opening in the body, termed an ostomy, that allows for discharge of body waste. The surgery includes preparation of a stoma, corresponding to the end of an organ such as the colon, small intestine, or ureter, that protrudes through the abdominal wall and through which the body waste is discharged. An ostomy appliance can be attached to a skin surface around the ostomy, termed a peristomal skin surface, for collection of the body waste.

Various types of ostomy appliances have been disclosed. For example, Fenton, U.S. Pat. No. 6,790,200, discloses an ostomy appliance and a mounting disc that include an ostomy pouch having a stoma receiving portal. The mounting disc is sealed about the portal and includes a flexible plastic disc having a convex central body portion and a surrounding annular rim. A first foam disc having an outer diameter corresponding to the outer diameter of the rim is adhesively adhered to the plastic disc. A second foam disc is adhered to an adhesive face of the first foam disc and has an outer diameter greater than the plastic disc. A hydrocolloid skin shield disc having an outer diameter corresponding to the outer diameter of the second foam disc is adhesively adhered to an adhesive face of the second disc.

Also for example, Fenton, U.S. Pat. No. 8,328,779, discloses a mounting assembly for an ostomy pouch. The assembly includes a body flange having an adhesive coating on one side adapted to be adhered to the peristomal skin surface of an ostomate. Diametrically opposed loops project from the edge of the flange and form pockets. An ostomy pouch having a stoma receiving opening surrounded by a stiffly flexible ring having diametrically opposed loops that cooperate with the pockets on the flange loops is also disclosed. An adhesive coating is provided on the flexible ring and flange. When the loops on the flexible ring are aligned with the pockets on the flange, the flange and ring may be adhesively interlocked to attach the pouch to the body flange.

Much effort has been invested in improving ostomy appliances, and in developing accessories, to make use of ostomy appliances as comfortable as possible. Yet ostomates still may have difficulty initially identifying an ostomy appliance that provides a suitable fit and still may be reluctant to try different ostomy appliances based on concern that a different fit will not be suitable.

Accordingly, a need exists for ostomy appliances that can provide improved fit and increased comfort for ostomates generally.

BRIEF SUMMARY OF THE INVENTION

A mounting assembly for an ostomy appliance is disclosed. The mounting assembly comprises a body flange. The body flange comprises a flexible plastic member located on a first side of the body flange. The flexible plastic member comprises a flange ring projecting axially from the body flange. The flexible plastic member also comprises a rim surrounding the flange ring. The flexible plastic member also comprises first and second loops extending radially from the rim. Each of the first and second loops comprises a raised fence around an opening that forms a pocket. The body flange also comprises an adhesive skin barrier member located on an opposite second side of the body flange. The mounting assembly also comprises an ostomy pouch. The ostomy pouch comprises a proximal sheet having an aperture. The ostomy pouch also comprises a distal sheet sealed to the proximal sheet at their respective peripheries to form the ostomy pouch. The ostomy pouch also comprises a pouch ring attached to the proximal sheet, surrounding the aperture of the proximal sheet. The pouch ring comprises an adhesive coating on the pouch ring. The pouch ring also comprises third and fourth loops extending radially from the pouch ring. The body flange and ostomy pouch are configured for the third and fourth loops to engage within the pocket of the first and second loops, respectively, the pouch ring to fit around the flange ring, and the rim of the flexible plastic member to contact the adhesive coating on the pouch ring, for assembly of the ostomy appliance. The adhesive skin barrier member has a multi-petaled outer perimeter that has a shape corresponding to 2 to 8 petals extending radially from the adhesive skin barrier member, distributed uniformly around the adhesive skin barrier member, and separated by notches that expand radially from the adhesive skin barrier member.

In accordance with some examples, the flexible plastic member further comprises a central dome.

Also in accordance with some examples, the body flange further comprises (a) a first double-sided adhesive substrate member adhered to the flexible plastic member opposite the flange ring, and having a size smaller than the multi-petaled outer perimeter of the adhesive skin barrier member, and (b) a second double-sided adhesive substrate member adhered to the first double-sided adhesive substrate member and the adhesive skin barrier member and having a multi-petaled outer perimeter that substantially corresponds in size and shape to the multi-petaled outer perimeter of the adhesive skin barrier member.

Also in accordance with some examples, the 2 to 8 petals each have a width that first increases, then decreases, radially outwardly from the adhesive skin barrier member.

Also in accordance with some examples, the adhesive skin barrier member has a maximum radius, and at least 50% of the multi-petaled outer perimeter of the adhesive skin barrier member extends to the maximum radius of the adhesive skin barrier member.

Also in accordance with some examples, the shape of the multi-petaled outer perimeter of the adhesive skin barrier member corresponds to 3 to 6 petals.

Also in accordance with some examples, the rim of the flexible plastic member is substantially annular.

Also in accordance with some examples, the first and second loops are diametrically opposed, and the third and fourth loops are diametrically opposed.

Also in accordance with some examples, the adhesive skin barrier member comprises an elastomer hydrocolloid mixture.

Also in accordance with some examples, the mounting assembly further comprises a first removable protective film covering the adhesive skin barrier member, and a second removable protective film covering the adhesive coating on the pouch ring.

Also in accordance with some examples, the flexible plastic member and the adhesive skin barrier member each have a stoma inlet portal, centrally positioned and extending therethrough.

An ostomy appliance also is disclosed. The ostomy appliance comprises a mounting assembly.

The mounting assembly comprises a body flange. The body flange comprises a flexible plastic member located on a first side of the body flange. The flexible plastic member comprises a flange ring projecting axially from the body flange. The flexible plastic member also comprises a rim surrounding the flange ring. The flexible plastic member also comprises first and second loops extending radially from the rim. Each of the first and second loops comprises a raised fence around an opening that forms a pocket. The body flange also comprises an adhesive skin barrier member located on an opposite second side of the body flange. The mounting assembly also comprises an ostomy pouch. The ostomy pouch comprises a proximal sheet having an aperture. The ostomy pouch also comprises a distal sheet sealed to the proximal sheet at their respective peripheries to form the ostomy pouch. The ostomy pouch also comprises a pouch ring attached to the proximal sheet, surrounding the aperture of the proximal sheet. The pouch ring comprises an adhesive coating on the pouch ring. The pouch ring also comprises third and fourth loops extending radially from the pouch ring. The body flange and ostomy pouch are configured for the third and fourth loops to engage within the pocket of the first and second loops, respectively, the pouch ring to fit around the flange ring, and the rim of the flexible plastic member to contact the adhesive coating on the pouch ring, for assembly of the ostomy appliance. The adhesive skin barrier member has a multi-petaled outer perimeter that has a shape corresponding to 2 to 8 petals extending radially from the adhesive skin barrier member, distributed uniformly around the adhesive skin barrier member, and separated by notches that expand radially from the adhesive skin barrier member.

The body flange and the ostomy pouch are in assembled engagement based on the third and fourth loops engaging within the pocket of the first and second loops, respectively, the pouch ring fitting around the flange ring, and the rim of the flexible plastic member contacting the adhesive coating on the pouch ring.

Also disclosed is a method of adhering an ostomy appliance to an ostomate at a peristomal skin surface of the ostomate. In accordance with the method, the ostomy appliance comprises a mounting assembly.

The mounting assembly comprises a body flange. The body flange comprises a flexible plastic member located on a first side of the body flange. The flexible plastic member comprises a flange ring projecting axially from the body flange. The flexible plastic member also comprises a rim surrounding the flange ring. The flexible plastic member also comprises first and second loops extending radially from the rim. Each of the first and second loops comprises a raised fence around an opening that forms a pocket. The body flange also comprises an adhesive skin barrier member located on an opposite second side of the body flange. The mounting assembly also comprises an ostomy pouch. The ostomy pouch comprises a proximal sheet having an aperture. The ostomy pouch also comprises a distal sheet sealed to the proximal sheet at their respective peripheries to form the ostomy pouch. The ostomy pouch also comprises a pouch ring attached to the proximal sheet, surrounding the aperture of the proximal sheet. The pouch ring comprises an adhesive coating on the pouch ring. The pouch ring also comprises third and fourth loops extending radially from the pouch ring. The body flange and ostomy pouch are configured for the third and fourth loops to engage within the pocket of the first and second loops, respectively, the pouch ring to fit around the flange ring, and the rim of the flexible plastic member to contact the adhesive coating on the pouch ring, for assembly of the ostomy appliance. The adhesive skin barrier member has a multi-petaled outer perimeter that has a shape corresponding to 2 to 8 petals extending radially from the adhesive skin barrier member, distributed uniformly around the adhesive skin barrier member, and separated by notches that expand radially from the adhesive skin barrier member.

The flexible plastic member and the adhesive skin barrier member each have a stoma inlet portal, centrally positioned and extending therethrough.

The method comprises a step of (1) placing the adhesive skin barrier member at the peristomal region of the ostomate, such that the stoma inlet portals of the flexible plastic member and the adhesive skin barrier member are aligned with a stoma of the ostomate. The method also comprises a step of (2) engaging the third loop with the pocket of the first loop. The method also comprises a step of (3) fitting the pouch ring around the flange ring. The method also comprises a step of (4) engaging the fourth loop with the pocket of the second loop. The method also comprises a step of (5) contacting the rim of the flexible plastic member to the adhesive coating on the pouch ring. In accordance with the method, the ostomy appliance is thereby adhered to the ostomate at the peristomal skin surface of the ostomate.

In accordance with some examples, the mounting assembly further comprises a first removable protective film covering the adhesive skin barrier member, and a second removable protective film covering the adhesive coating on the pouch ring. In accordance with these examples, the method further comprises a step of removing the first removable protective film from the adhesive skin barrier member prior to step (1), and a step of removing the second removable protective film from the adhesive coating on the pouch ring prior to steps (2) to (5).

Also in accordance with some examples, the ostomy appliance adheres to the ostomate at the peristomal skin surface of the ostomate with a smooth fit.

Also in accordance with some examples, the ostomy appliance adheres to the ostomate at the peristomal skin surface of the ostomate without application of adhesive tape to the ostomy appliance or to the ostomate.

Also disclosed is another method of adhering an ostomy appliance to an ostomate at a peristomal skin surface of the ostomate. In accordance with the method, the ostomy appliance comprises a mounting assembly.

The mounting assembly comprises a body flange. The body flange comprises a flexible plastic member located on a first side of the body flange. The flexible plastic member comprises a flange ring projecting axially from the body flange. The flexible plastic member also comprises a rim surrounding the flange ring. The flexible plastic member also comprises first and second loops extending radially from the rim. Each of the first and second loops comprises a raised fence around an opening that forms a pocket. The body flange also comprises an adhesive skin barrier member located on an opposite second side of the body flange. The mounting assembly also comprises an ostomy pouch. The ostomy pouch comprises a proximal sheet having an aperture. The ostomy pouch also comprises a distal sheet sealed to the proximal sheet at their respective peripheries to form the ostomy pouch. The ostomy pouch also comprises a pouch ring attached to the proximal sheet, surrounding the aperture of the proximal sheet. The pouch ring comprises an adhesive coating on the pouch ring. The pouch ring also comprises third and fourth loops extending radially from the pouch ring. The body flange and ostomy pouch are configured for the third and fourth loops to engage within the pocket of the first and second loops, respectively, the pouch ring to fit around the flange ring, and the rim of the flexible plastic member to contact the adhesive coating on the pouch ring, for assembly of the ostomy appliance. The adhesive skin barrier member has a multi-petaled outer perimeter that has a shape corresponding to 2 to 8 petals extending radially from the adhesive skin barrier member, distributed uniformly around the adhesive skin barrier member, and separated by notches that expand radially from the adhesive skin barrier member.

The method comprises a step of (0) cutting a stoma inlet portal through at least the adhesive skin barrier member, such that the flexible plastic member and the adhesive skin barrier member each have a stoma inlet portal, centrally positioned and extending therethrough. The method also comprises a step of (1) placing the adhesive skin barrier member at the peristomal region of the ostomate, such that the stoma inlet portals of the flexible plastic member and the adhesive skin barrier member are aligned with a stoma of the ostomate. The method also comprises a step of (2) engaging the third loop with the pocket of the first loop. The method also comprises a step of (3) fitting the pouch ring around the flange ring. The method also comprises a step of (4) engaging the fourth loop with the pocket of the second loop. The method also comprises a step of (5) contacting the rim of the flexible plastic member to the adhesive coating on the pouch ring. In accordance with the method, the ostomy appliance is thereby adhered to the ostomate at the peristomal skin surface of the ostomate.

In accordance with some examples, the mounting assembly further comprises a first removable protective film covering the adhesive skin barrier member, and a second removable protective film covering the adhesive coating on the pouch ring. In accordance with these examples, the method further comprises a step of removing the first removable protective film from the adhesive skin barrier member prior to steps (0) and (1), and a step of removing the second removable protective film from the adhesive coating on the pouch ring prior to steps (2) to (5).

Also in accordance with some examples, the ostomy appliance adheres to the ostomate at the peristomal skin surface of the ostomate with a smooth fit.

Also in accordance with some examples, the ostomy appliance adheres to the ostomate at the peristomal skin surface of the ostomate without application of adhesive tape to the ostomy appliance or to the ostomate.

BRIEF DESCRIPTION OF THE DRAWINGS

These and other features, aspects, and advantages of the claimed mounting assemblies, ostomy appliances, and methods are better understood when the following detailed description is read with reference to the accompanying drawings, in which:

DETAILED DESCRIPTION OF THE INVENTION

Figure 1:
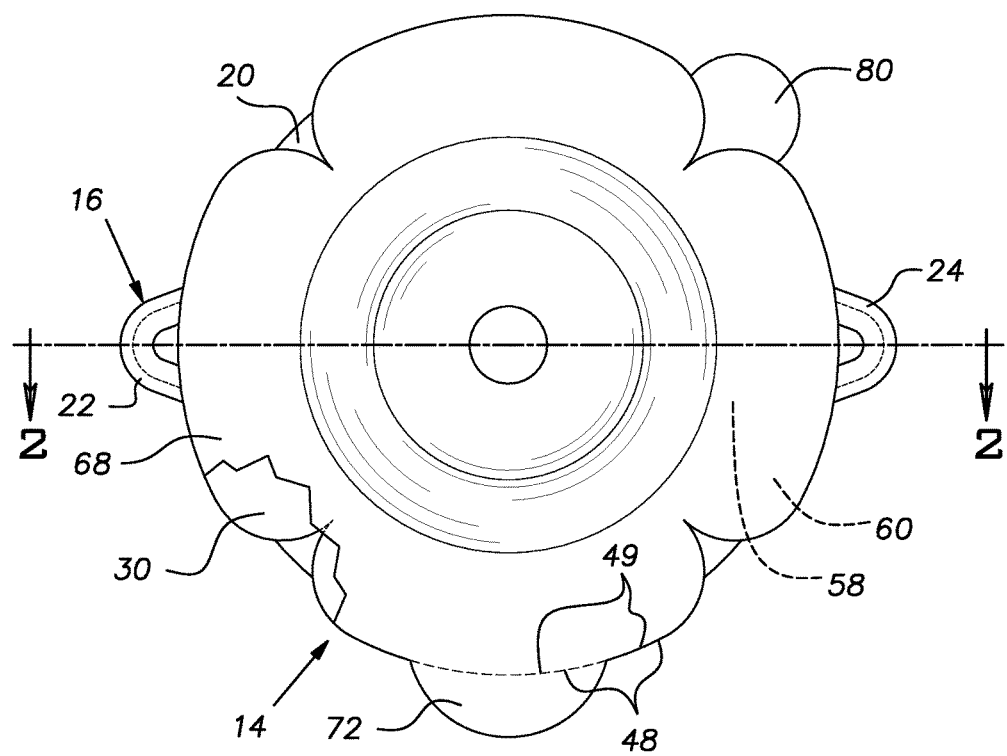
FIG. 1 is a top plan view of a body flange of a mounting assembly for an ostomy appliance as disclosed.
Figure 2:
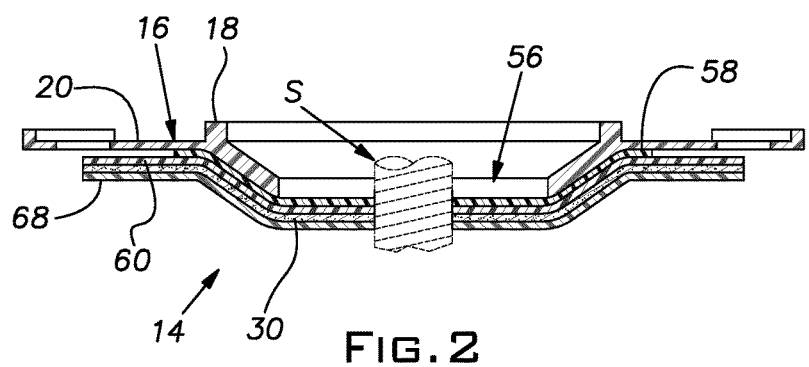
FIG. 2 is an inverted sectional view, the plane of the section being indicated by the line 2-2 in FIG. 1.
Figure 3:
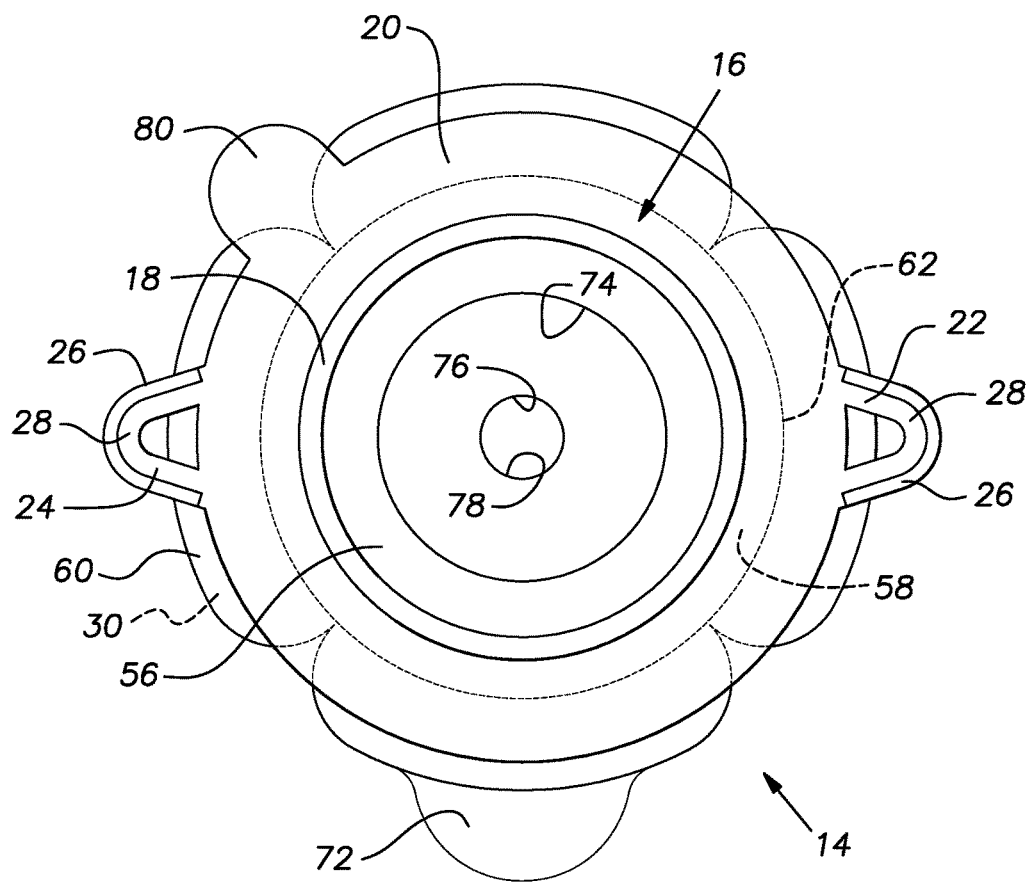
FIG. 3 is a bottom plan view of a body flange of a mounting assembly for an ostomy appliance as disclosed.

A mounting assembly for an ostomy appliance 12 is disclosed (FIG. 1 to FIG. 7). The mounting assembly comprises a body flange 14 (FIG. 1, FIG. 2, and FIG. 3). The body flange 14 comprises a flexible plastic member 16 located on a first side of the body flange 14. The flexible plastic member 16 comprises a flange ring 18 projecting axially from the body flange 14. The flexible plastic member 16 also comprises a rim 20 surrounding the flange ring 18. The flexible plastic member 16 also comprises first and second loops 22, 24 extending radially from the rim 20. Each of the first and second loops 22, 24 comprises a raised fence 26 around an opening that forms a pocket 28. The body flange 14 also comprises an adhesive skin barrier member 30 located on an opposite second side of the body flange 14.

Figures 4, 5:
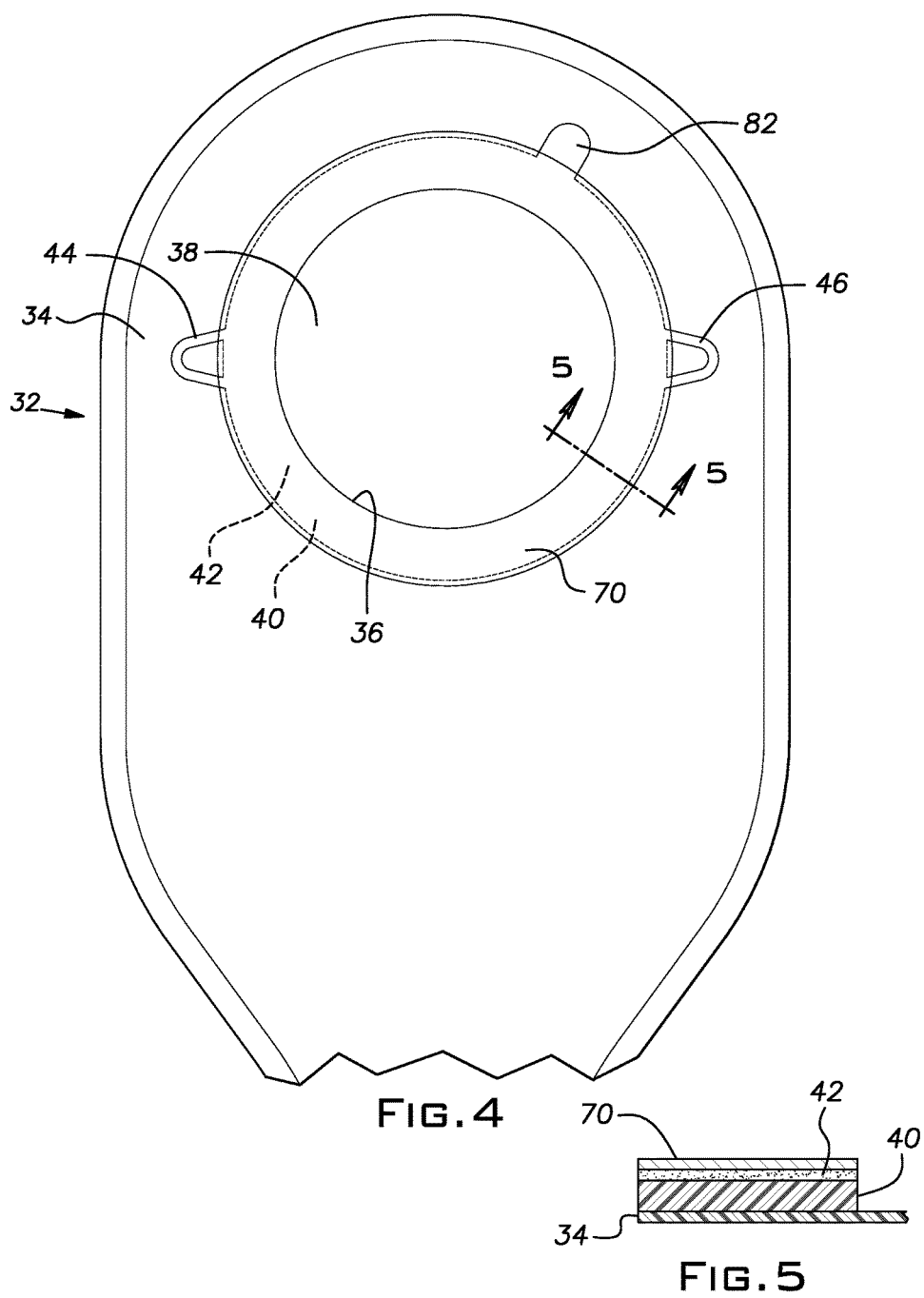
FIG. 4 is a front elevational view of an ostomy pouch of a mounting assembly for an ostomy appliance as disclosed.
FIG. 5 is a sectional view, the plane of the section being indicated by the line 5-5 in FIG. 4.

The mounting assembly also comprises an ostomy pouch 32 (FIG. 4 and FIG. 5). The ostomy pouch 32 comprises a proximal sheet 34 having an aperture 36. The ostomy pouch 32 also comprises a distal sheet 38 sealed to the proximal sheet 34 at their respective peripheries to form the ostomy pouch 32. The ostomy pouch 32 also comprises a pouch ring 40 attached to the proximal sheet 34, surrounding the aperture 36 of the proximal sheet 34. The pouch ring 40 comprises an adhesive coating 42 on the pouch ring 40. The pouch ring 40 also comprises third and fourth loops 44, 46 extending radially from the pouch ring 40.

Figure 7:
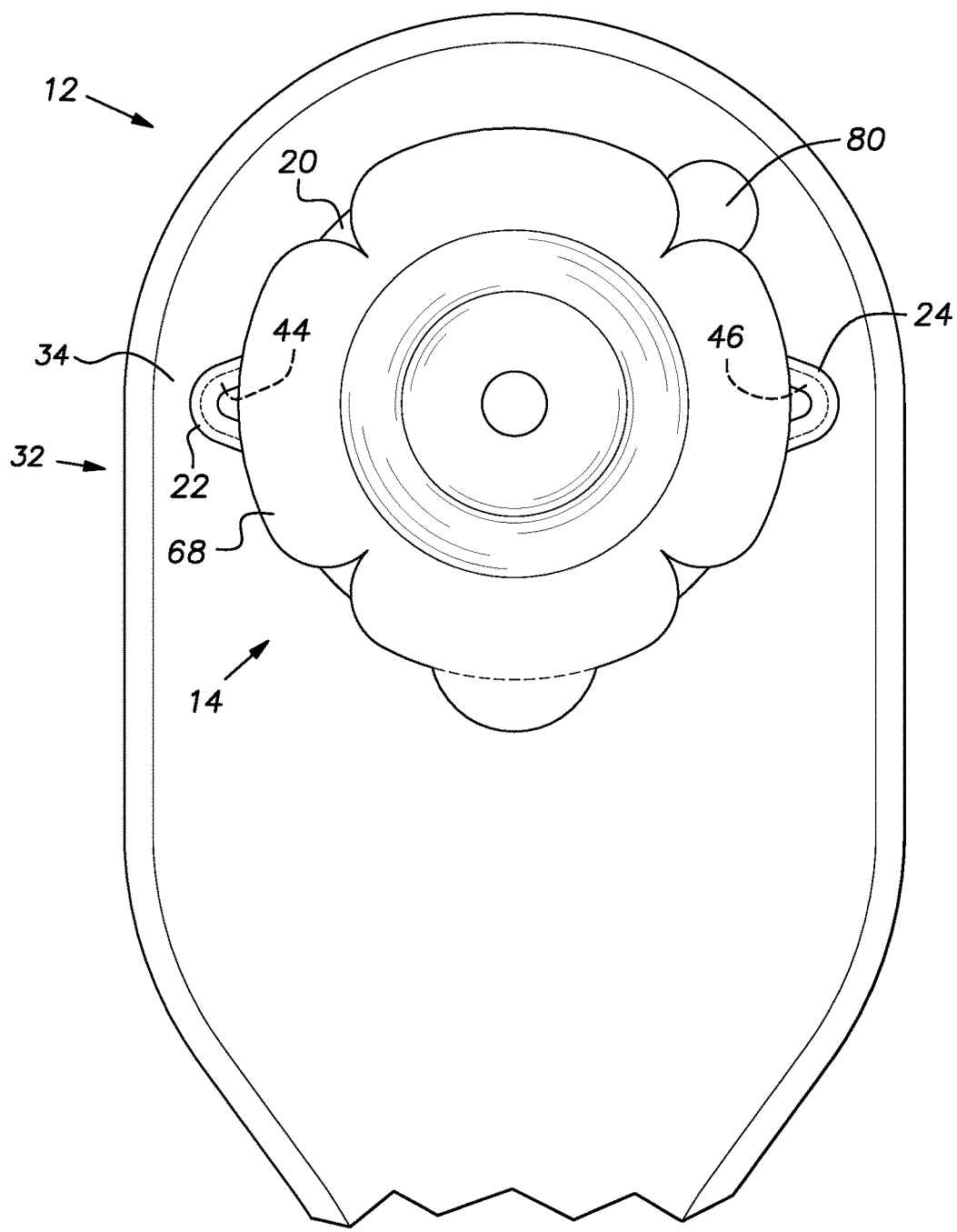
FIG. 7 is a front elevational view of an ostomy appliance assembled as disclosed.
Figure 8:
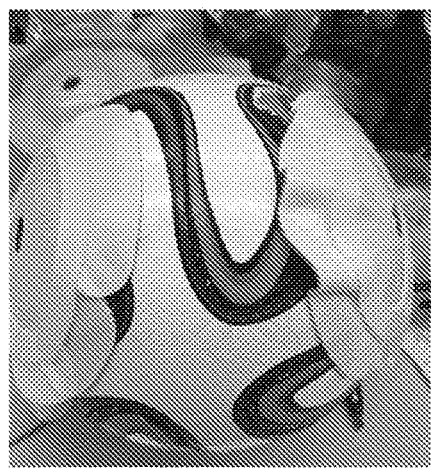
FIG. 8 shows photographs of a multi-petaled body flange of a mounting assembly for an ostomy appliance and a circular (non-multi-petaled) body flange of a mounting assembly for an ostomy appliance applied to a curved surface of a ball (A) immediately after application and (B) approximately 24 hours after application.
Figure 8:
Figure 9:
FIG. 9 shows photographs of a multi-petaled body flange of a mounting assembly for an ostomy appliance and a circular (non-multi-petaled) body flange of a mounting assembly for an ostomy appliance applied to a curved surface of a vase (A) immediately after application and (B) approximately 24 hours after application.
Figure 9:
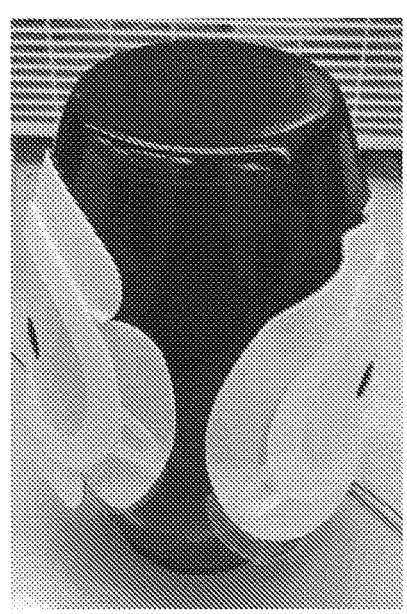
Figure 10:
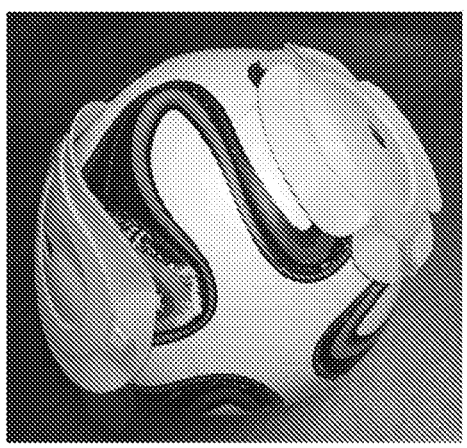
FIG. 10 shows photographs of a multi-petaled body flange of a mounting assembly for an ostomy appliance and a circular (non-multi-petaled) body flange of a mounting assembly for an ostomy appliance applied to a curved surface of a ball (A) immediately after application and (B) approximately 24 hours after application.
Figure 10:
Figure 11:
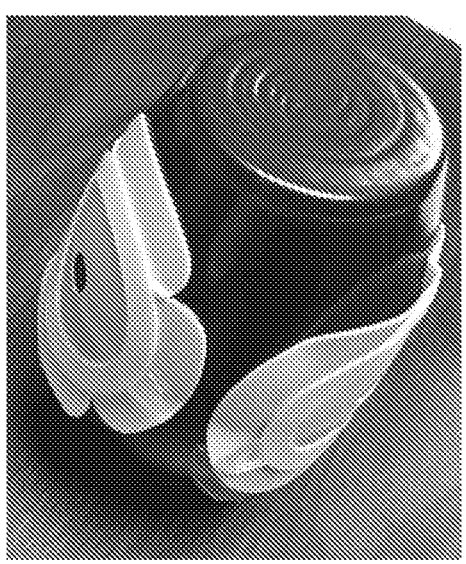
FIG. 11 shows photographs of a multi-petaled body flange of a mounting assembly for an ostomy appliance and a circular (non-multi-petaled) body flange of a mounting assembly for an ostomy appliance applied to a curved surface of a vase (A) immediately after application and (B) approximately 24 hours after application.
Figure 11:
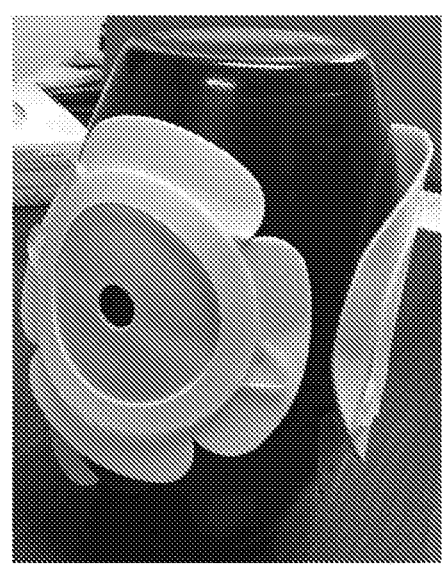

The body flange 14 and ostomy pouch 32 are configured for the third and fourth loops 44, 46 to engage within the pocket 28 of the first and second loops 22, 24, respectively, the pouch ring 40 to fit around the flange ring 18, and the rim 20 of the flexible plastic member 16 to contact the adhesive coating 42 on the pouch ring 40, for assembly of the ostomy appliance 12 (FIG. 1, FIG. 4, and FIG. 7).

Figure 6:
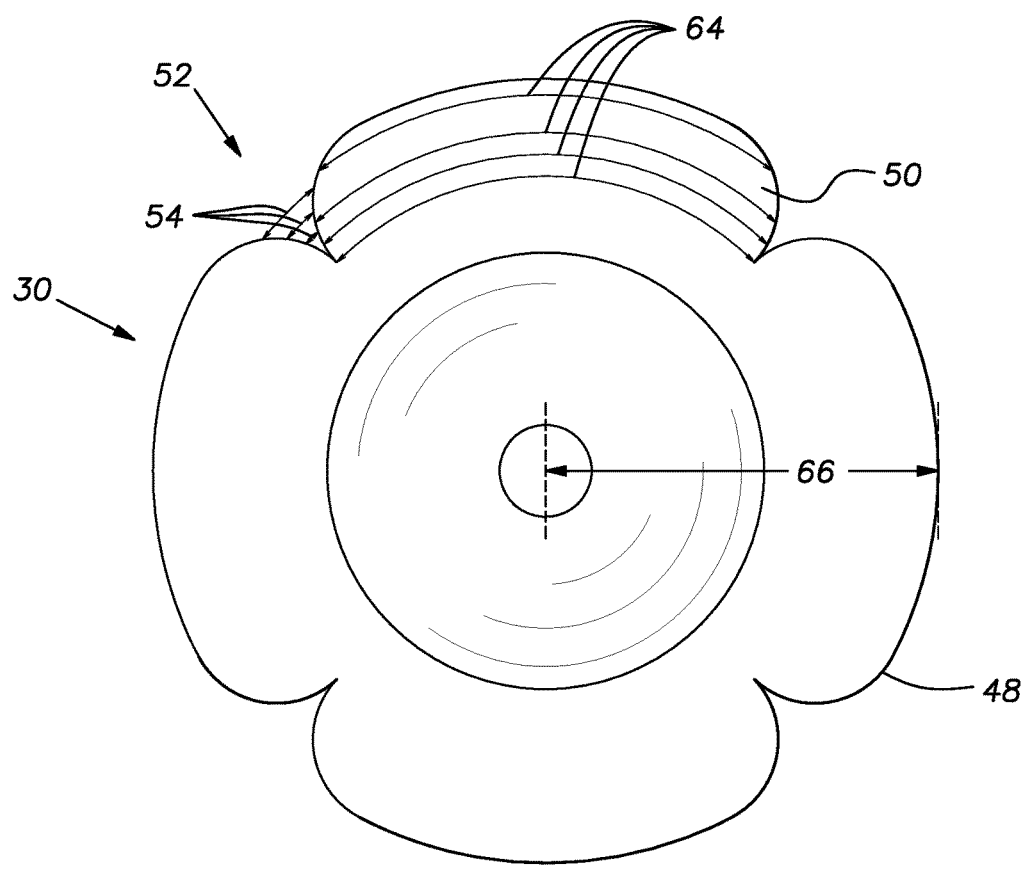
FIG. 6 is a top plan view of an adhesive skin barrier member of a body flange of a mounting assembly for an ostomy appliance as disclosed.

The adhesive skin barrier member 30 has a multi-petaled outer perimeter 48 that has a shape corresponding to 2 to 8 petals 50 extending radially from the adhesive skin barrier member 30, distributed uniformly around the adhesive skin barrier member 30, and separated by notches 52 that expand radially from the adhesive skin barrier member 30 (FIG. 6).

The mounting assembly provides improved fit of the adhesive skin barrier member 30 at a peristomal region of an ostomate, e.g. such that a corresponding ostomy appliance 12 adheres to the ostomate at the peristomal skin surface of the ostomate with a smooth fit and/or that the ostomy appliance 12 adheres to the ostomate at the peristomal skin surface of the ostomate without need for application of adhesive tape to the ostomy appliance 12 or to the ostomate. The size and shape of the multi-petaled outer perimeter 48 of the adhesive skin barrier member 30 of the body flange 14 allows the adhesive skin barrier member 30 to be adapted to a peristomal skin surface of an ostomate, without undesirable bunching upon application, and this applies across a range of peristomal skin surface contours of ostomates, e.g. for ostomates with peristomal skin surfaces that are flat, curved, bulging, and/or irregular. Thus, this configuration provides improved fit and increased comfort for ostomates generally. As the pouch fills with body waste, the adhesive skin barrier member 30 will remain secure and stay attached at the peristomal skin surface of the ostomate, and not peel away. Moreover, the mounting assembly allows an ostomate to change ostomy pouches 32 multiple times without having to remove the body flange 14 from the peristomal skin surface of the ostomate.

As noted, the mounting assembly comprises a body flange 14 (FIG. 1, FIG. 2, and FIG. 3). The body flange 14 comprises a flexible plastic member 16. The flexible plastic member 16 can be made from, for example, a copolymer of ethylene and vinyl acetate, e.g. the ELVAX® 450 product of DuPont. The flexible plastic member 16 is located on a first side of the body flange 14.

The flexible plastic member 16 comprises a flange ring 18 projecting axially, e.g. along a major axis, from the body flange 14. The flange ring 18 can have an inner diameter of, for example, 50 to 75 mm, 55 to 70 mm, 58 to 65 mm, or about 61 mm. The flange ring 18 can have an outer diameter of, for example, 55 to 85 mm, 60 to 80 mm, 63 to 75 mm, or about 68 mm. The flange ring 18 can have a radial width of, for example, 1 to 10 mm, 2 to 5 mm, or about 3 mm. The flange ring 18 can project axially, for example, 0.5 to 10 mm, 1 to 5 mm, or about 2 mm.

The flexible plastic member 16 also comprises a rim 20 surrounding the flange ring 18. The rim 20 of the flexible plastic member 16 can have an outer diameter of, for example, 70 to 130 mm, 85 to 115 mm, 95 to 105 mm, or about 100 mm.

The flexible plastic member 16 also comprises first and second loops 22, 24 extending radially from the rim 20. Each of the first and second loops 22, 24 comprises a raised fence 26 around an opening that forms a pocket 28.

The body flange 14 also comprises an adhesive skin barrier member 30 located on an opposite second side of the body flange 14. The adhesive skin barrier member 30 can be made from a suitable material for providing a skin barrier, can be pliable, and can have both dry tack and wet tack.

The mounting assembly also comprises an ostomy pouch 32 (FIG. 4 and FIG. 5). The ostomy pouch 32 can be designed for single use, e.g. by not having an opening for draining contents of the ostomy pouch 32, or for multiple use, e.g. by having an opening for draining contents of the ostomy pouch 32.

The ostomy pouch 32 comprises a proximal sheet 34 having an aperture 36. The aperture 36 can have a diameter of, for example, 55 to 85 mm, 60 to 80 mm, 63 to 75 mm, or about 68 mm.

The ostomy pouch 32 also comprises a distal sheet 38 sealed to the proximal sheet 34 at their respective peripheries to form the ostomy pouch 32.

The ostomy pouch 32 also comprises a pouch ring 40 attached to the proximal sheet 34, surrounding the aperture 36 of the proximal sheet 34. The pouch ring 40 can be made from a plastic and can be flexible. The pouch ring 40 can be attached to the proximal sheet 34, for example based on an adhesive. The pouch ring 40 can surround the aperture 36 of the proximal sheet 34, for example based on the pouch ring 40 having an inner diameter and the aperture 36 of the proximal sheet 34 having an diameter, the inner diameter of the pouch ring 40 being greater than or equal to the diameter of the aperture 36 of the proximal sheet 34. The pouch ring 40 also can surround the aperture 36 of the proximal sheet 34, for example based on the pouch ring 40 being attached to the proximal sheet 34 at a portion of the proximal sheet 34 surrounding the aperture 36.

The pouch ring 40 comprises an adhesive coating 42 on the pouch ring 40.

The pouch ring 40 also comprises third and fourth loops 44, 46 extending radially from the pouch ring 40.

The body flange 14 and ostomy pouch 32 are configured for the third and fourth loops 44, 46 to engage within the pocket 28 of the first and second loops 22, 24, respectively, the pouch ring 40 to fit around the flange ring 18, and the rim 20 of the flexible plastic member 16 to contact the adhesive coating 42 on the pouch ring 40, for assembly of the ostomy appliance 12. Engagement of the third and fourth loops 44, 46 within the pocket 28 of the first and second loops 22, 24, respectively, and fitting of the pouch ring 40 around the flange ring 18, serve to locate the ostomy pouch 32 onto the body flange 14. Contacting the rim 20 of the flexible plastic member 16 to the adhesive coating 42 on the pouch ring 40 completes an adhesive bond between the ostomy pouch 32 and the body flange 14.

The adhesive skin barrier member 30 has a multi-petaled outer perimeter 48 that has a shape corresponding to 2 to 8 petals 50 extending radially from the adhesive skin barrier member 30, distributed uniformly around the adhesive skin barrier member 30, and separated by notches 52 that expand radially from the adhesive skin barrier member 30 (FIG. 6). For example, the multi-petaled outer perimeter 48 of the adhesive skin barrier member 30 can have a shape corresponding to 2 to 8 petals 50 extending radially from the adhesive skin barrier member 30, distributed uniformly around the adhesive skin barrier member 30, and separated by notches 52 that expand radially from the adhesive skin barrier member 30, such that the adhesive skin barrier member 30 has a center, and each of the 2 to 8 petals 50 extend radially with respect to the center of the adhesive skin barrier member 30. Also for example, the multi-petaled outer perimeter 48 of the adhesive skin barrier member 30 can have a shape corresponding to 2 to 8 petals 50 extending radially from the adhesive skin barrier member 30, distributed uniformly around the adhesive skin barrier member 30, and separated by notches 52 that expand radially from the adhesive skin barrier member 30, such that each of the 2 to 8 petals 50 is substantially identical in size and that each of the 2 to 8 petals 50 is positioned equidistant from the petals 50 adjacent thereto. Also for example, the multi-petaled outer perimeter 48 of the adhesive skin barrier member 30 can have a shape corresponding to 2 to 8 petals 50 extending radially from the adhesive skin barrier member 30, distributed uniformly around the adhesive skin barrier member 30, and separated by notches 52 that expand radially from the adhesive skin barrier member 30, such that each of the 2 to 8 petals 50 is separated from the petals 50 adjacent thereto by a notch 52 on either side thereof, each notch 52 having a notch width 54, measured as an arcuate length with respect to the center of the adhesive skin barrier member 30, that increases with increasing distance from the center of the adhesive skin barrier member 30.

In accordance with some examples, the flexible plastic member 16 further comprises a central dome 56 (FIG. 1, FIG. 2, and FIG. 3). The central dome 56 can be oriented axially inwardly with respect to the body flange 14, such that the flexible plastic member 16 is convex on a side of the flexible plastic member 16 opposite the side from which the flange ring 18 projects. For example, the central dome 56 can have a convexity of, for example, 2 to 15 mm, 4 to 12 mm, 5 to 11 mm, or 6 to 10 mm. Also for example, the central dome 56 can have a convexity of, for example, 2 mm, 3 mm, 4 mm, 5 mm, 6 mm, 7 mm, 8 mm, 9 mm, 10 mm, 11 mm, 12 mm, 13 mm, 14 mm, or 15 mm. In accordance with these examples, the central dome 56 can have a shape of, for example, a spherical cap, e.g. a dome with a rounded top, or a spherical segment, e.g. a dome with a flat top, among other shapes. Also in accordance with these examples, to the extent that the central dome 56 is convex, then, following assembly of the body flange 14, corresponding overlapping portions of the adhesive skin barrier member 30 are also convex, and thus then the body flange 14 is also convex in corresponding portions thereof.

Also in accordance with some examples, the body flange 14 further comprises (a) a first double-sided adhesive substrate member 58 adhered to the flexible plastic member 16 opposite the flange ring 18, and having a size smaller than the multi-petaled outer perimeter 48 of the adhesive skin barrier member 30, and (b) a second double-sided adhesive substrate member 60 adhered to the first double-sided adhesive substrate member 58 and the adhesive skin barrier member 30 and having a multi-petaled outer perimeter 49 that substantially corresponds in size and shape to the multi-petaled outer perimeter 48 of the adhesive skin barrier member 30.

In accordance with these examples, the first double-sided adhesive substrate member 58 can be made from, for example, a foam layer, a thermoplastic layer, a polypropylene layer, a polyethylene layer, a nonwoven layer, and/or a film layer. Also, the first double-sided adhesive substrate member 58 can be a soft, resilient double-sided adhesive substrate member. Thus, in some examples the first double-sided adhesive substrate member 58 can comprise a foam layer, e.g. a soft, resilient foam layer.

Also in accordance with these examples, the second double-sided adhesive substrate member 60 also can be made from, for example, a foam layer, a thermoplastic layer, a polypropylene layer, a polyethylene layer, a nonwoven layer, and/or a film layer. Also, the second double-sided adhesive substrate member 60 can be a soft, resilient double-sided adhesive substrate member. Thus, in some examples the second double-sided adhesive substrate member 60 can comprise a foam layer, e.g. a soft, resilient foam layer.

Also in accordance with these examples, the first double-sided adhesive substrate member 58 can be adhered to the flexible plastic member 16 opposite the flange ring 18, e.g. based on use of a pressure-sensitive adhesive layer, such that the first double-sided adhesive substrate member 58 is adhered to the flexible plastic member 16 on a side of the flexible plastic member 16 opposite the side from which the flange ring 18 projects.

Also in accordance with these examples, the second double-sided adhesive substrate member 60 can be adhered to the first double-sided adhesive substrate member 58 and the adhesive skin barrier member 30, e.g. also based on use of a pressure-sensitive adhesive layer, such that the second double-sided adhesive substrate member 60 is adhered to the first double-sided adhesive substrate member 58 on a side of the first double-sided adhesive substrate member 58 opposite the side adhered to the flexible plastic member 16, and to the adhesive skin barrier member 30 on a side of the adhesive skin barrier member 30 oriented toward the flexible plastic member 16.

Also in accordance with these examples, with respect to size, for example the first double-sided adhesive substrate member 58 can have a size smaller than the multi-petaled outer perimeter 48 of the adhesive skin barrier member 30 such that when the adhesive skin barrier member 30 is positioned on the first double-sided adhesive substrate member 58 and is centered with respect thereto, the multi-petaled outer perimeter 48 of the adhesive skin barrier member 30 extends at least, for example, 5 to 25 mm, 8 to 20 mm, or 10 to 15 mm, beyond an outer perimeter 62 of the first double-sided adhesive substrate member 58 along at least 50% of the multi-petaled outer perimeter 48 of the adhesive skin barrier member 30. Also for example, the first double-sided adhesive substrate member 58 can have a size smaller than the multi-petaled outer perimeter 48 of the adhesive skin barrier member 30 such that when the adhesive skin barrier member 30 is positioned on the first double-sided adhesive substrate member 58 and is centered with respect thereto, the multi-petaled outer perimeter 48 of the adhesive skin barrier member 30 extends at least, for example, 0.2 to 25 mm, 0.5 to 20 mm, or 1 to 15 mm, beyond an outer perimeter 62 of the first double-sided adhesive substrate member 58 along at least 95%, at least 98%, or 100% of the multi-petaled outer perimeter 48 of the adhesive skin barrier member 30.

Also in accordance with these examples, the notches 52 can expand radially from the adhesive skin barrier member 30, starting from a distance radially beyond an outer perimeter 62 of the first double-sided adhesive substrate member 58, e.g. a distance of 0.5 to 5 mm, 0.8 to 3 mm, or 1 to 2 mm, radially beyond an outer perimeter 62 of the first double-sided adhesive substrate member 58. In accordance with these examples, during use of the ostomy appliance 12 as adhered to an ostomate, this configuration may provide additional improved fit based on formation of small tears in the adhesive skin barrier member 30 and the second double-sided adhesive substrate member 60, extending from the notches 52 radially inwardly toward the outer perimeter 62 of first double-sided adhesive substrate member 58.

Also in accordance with these examples, the second double-sided adhesive substrate member 60 can have a multi-petaled outer perimeter 49 that substantially corresponds in size and shape to the multi-petaled outer perimeter 48 of the adhesive skin barrier member 30 such that when the adhesive skin barrier member 30 is positioned on the second double-sided adhesive substrate member 60 in an orientation maximizing alignment thereof, the multi-petaled outer perimeter 48 of the adhesive skin barrier member 30 extends not more than, for example, 10 mm, 3 mm, or 1 mm beyond the multi-petaled outer perimeter 49 of the second double-sided adhesive substrate member 60 at any point along the multi-petaled outer perimeter 48 of the adhesive skin barrier member 30. Also for example, the multi-petaled outer perimeter 48 of the adhesive skin barrier member 30 can correspond in size and shape to the multi-petaled outer perimeter 49 of the second double-sided adhesive substrate member 60 such that when the adhesive skin barrier member 30 is positioned on the second double-sided adhesive substrate member 60 in an orientation maximizing alignment thereof, the multi-petaled outer perimeter 49 of the second double-sided adhesive substrate member 60 extends not more than, for example, 10 mm, 3 mm, or 1 mm beyond the multi-petaled outer perimeter 48 of the adhesive skin barrier member 30 at any point along the multi-petaled outer perimeter 49 of the second double-sided adhesive substrate member 60. Also for example, the multi-petaled outer perimeter 48 of the adhesive skin barrier member 30 can correspond in size and shape to the multi-petaled outer perimeter 49 of the second double-sided adhesive substrate member 60 such that the multi-petaled outer perimeter 48 of the adhesive skin barrier member 30 is identical in size and shape to the multi-petaled outer perimeter 49 of the second double-sided adhesive substrate member 60. The multi-petaled outer perimeter 49 of the second double-sided adhesive substrate member 60 also has a shape corresponding to 2 to 8 petals extending radially from the second double-sided adhesive substrate member 60, distributed uniformly around the second double-sided adhesive substrate member 60, and separated by notches that expand radially from the second double-sided adhesive substrate member 60.

Also in accordance with some examples, the 2 to 8 petals 50 each have a petal width 64 that first increases, then decreases, radially outwardly from the adhesive skin barrier member 30 (FIG. 6). For example, the 2 to 8 petals 50 each can have a petal width 64 that first increases, then decreases, radially outwardly from the adhesive skin barrier member 30, such that the adhesive skin barrier member 30 has a center, and the 2 to 8 petals 50 each have a petal width 64, measured as an arcuate length with respect to the center of the adhesive skin barrier member 30, that first increases, then decreases, with increasing distance from the center of the adhesive skin barrier member 30.

Also in accordance with some examples, the adhesive skin barrier member 30 has a maximum radius 66, and at least 50% of the multi-petaled outer perimeter 48 of the adhesive skin barrier member 30 extends to the maximum radius 66 of the adhesive skin barrier member 30. For example, the adhesive skin barrier member 30 can have a maximum radius 66, and at least 50% of the multi-petaled outer perimeter 48 of the adhesive skin barrier member 30 can extend to the maximum radius 66 of the adhesive skin barrier member 30, such that, for example, at least 50%, 60%, 70% or 80% of the multi-petaled outer perimeter 48 of the adhesive skin barrier member 30 extends to the same distance from the center of the adhesive skin barrier member 30 and no point on the multi-petaled outer perimeter 48 of the adhesive skin barrier member 30 extends further than this. In accordance with these examples, the second double-sided adhesive substrate member 60, if present, can also be dimensioned this way.

Also in accordance with some examples, the shape of the multi-petaled outer perimeter 48 of the adhesive skin barrier member 30 corresponds to 3 to 6 petals 50. For example, the shape of the multi-petaled outer perimeter 48 of the adhesive skin barrier member 30 can correspond, for example, to 3 petals 50, 4 petals 50, 5 petals 50, or 6 petals 50. In accordance with these examples, the second double-sided adhesive substrate member 60, if present, can also be dimensioned this way.

Also in accordance with some examples, the rim 20 of the flexible plastic member 16 is substantially annular (FIG. 3). For example, the rim 20 of the flexible plastic member 16 can be circular. In other examples, the rim 20 of the flexible plastic member 16 can have other shapes, e.g. oval, polygonal, etc.

Also in accordance with some examples, the first and second loops 22, 24 are diametrically opposed, and the third and fourth loops 44, 46 are diametrically opposed (FIG. 1, FIG. 4, and FIG. 7). The first and second loops 22, 24 and the third and fourth loops 44, 46 can be used to align the body flange 14 and the ostomy pouch 32 during assembly of the ostomy appliance 12.

Also in accordance with some examples, the adhesive skin barrier member 30 comprises an elastomer hydrocolloid mixture. The elastomer hydrocolloid mixture can include, for example, a Karaya-glycerine formulation, mixtures of polyacrylamide resins, and/or other polyols.

Also in accordance with some examples, the mounting assembly further comprises a first removable protective film 68 covering the adhesive skin barrier member 30, and a second removable protective film 70 covering the adhesive coating 42 on the pouch ring 40 (FIG. 1, FIG. 2, FIG. 4, and FIG. 5). In some examples, the first removable protective film 68 can include a part, such as a tab 72, that extends continuously beyond the multi-petaled outer perimeter 48 of the adhesive skin barrier member 30, and that can be used to remove the first removable protective film 68 from the adhesive skin barrier member 30.

Also in accordance with some examples, the flexible plastic member 16 and the adhesive skin barrier member 30 each have a stoma inlet portal 74, 76 respectively, centrally positioned and extending therethrough, which together form a stoma inlet portal 78 of the body flange 14 (FIG. 3). The stoma inlet portals 74, 76 of the flexible plastic member 16 and the adhesive skin barrier member 30, respectively, can have a size and shape suitable for a stoma (designated S in FIG. 2) of an ostomate. For example, the stoma inlet portals 74, 76 of the flexible plastic member 16 and the adhesive skin barrier member 30 can have a size corresponding to a diameter of, for example, 10 mm to 50 mm, e.g. about 12 to 13 mm, about 15 to 16 mm, about 22 to 23 mm, about 25 to 26 mm, about 28 to 29 mm, about 31 to 32 mm, about 34 to 35 mm, about 38 to 39 mm, about 41 to 42 mm, or about 44 to 45 mm. Also for example, the stoma inlet portals 74, 76 of the flexible plastic member 16 and the adhesive skin barrier member 30 can have a size corresponding to a diameter of, for example, 12.7 mm, 15.9 mm, 22.2 mm, 25.4 mm, 28.6 mm, 31.8 mm, 34.9 mm, 41.3 mm, or 44.5 mm. Also for example, the stoma inlet portals 74, 76 of the flexible plastic member 16 and the adhesive skin barrier member 30 can have a shape corresponding to a circle. Also for example, the stoma inlet portals 74, 76 of the flexible plastic member 16 and the adhesive skin barrier member 30 can have a shape that is cut to fit a stoma of an ostomate. Also for example, the first double-sided adhesive substrate member 58, if present, and the second double-sided adhesive substrate member 60, if present, also can each have a stoma inlet portal, respectively, centrally positioned and extending therethrough, which together also form the stoma inlet portal 78 of the body flange 14.

The body flange 14 and the ostomy pouch 32 of the mounting assembly can be assembled, to form the ostomy appliance 12, as follows (FIG. 7). The third and fourth loops 44, 46 can be engaged within the pocket 28 of the first and second loops 22, 24, respectively (FIG. 1 and FIG. 4). This can be done, for example, sequentially, e.g. based on engaging the third loop 44 within the pocket 28 of the first loop 22, then later engaging the fourth loop 46 within the pocket 28 of the second loop 24. This also can be done, for example, simultaneously, e.g. based on engaging the third loop 44 within the pocket 28 of the first loop 22, and simultaneously engaging the fourth loop 46 within the pocket 28 of the second loop 24. The engagement can align pouch ring 40 around the flange ring 18 (FIG. 2 and FIG. 4). The pouch ring 40 can then be fit around the flange ring 18, e.g. by snapping the pouch ring 40 in place around the flange ring 18. This puts the rim 20 of the flexible plastic member 16 adjacent the adhesive coating 42 on the pouch ring 40. The rim 20 of the flexible plastic member 16 can then be put in contact with the adhesive coating 42 on the pouch ring 40. This completes and adhesive bond between ostomy pouch 32 and the body flange 14. Other approaches for assembly of the body flange 14 and the ostomy pouch 32 to form the ostomy appliance 12 also can be used.

The ostomy appliance 12 also can be disassembled, to separate the ostomy pouch 32 from the body flange 14, e.g. to replace the ostomy pouch 32 as used with an ostomy pouch 32 that has not yet been used, as follows (FIG. 1, FIG. 4, and FIG. 7). In some examples, the rim 20 of the flexible plastic member 16 further comprises a tab 80 extending axially therefrom, and the pouch ring 40 also further comprises a tab 82 extending axially therefrom. In accordance with these examples, the tab 80 of the flexible plastic member 16 and the tab 82 of the pouch ring 40 can each be grasped independently. Then the tab 82 of the pouch ring 40 can be pulled, releasing the rim 20 of the flexible plastic member 16 from contact with the adhesive coating 42 on the pouch ring 40, releasing the pouch ring 40 from around the flange ring 18, and releasing the third and fourth loops 44, 46 from the pocket 28 of each of the first and second loops 22, 24. Other approaches for disassembly of the ostomy appliance 12 also can be used.

An ostomy appliance 12 also is disclosed (FIG. 7). The ostomy appliance 12 comprises a mounting assembly.

The mounting assembly is as described above. Accordingly, the mounting assembly comprises a body flange 14. The body flange 14 comprises a flexible plastic member 16 located on a first side of the body flange 14. The flexible plastic member 16 comprises a flange ring 18 projecting axially from the body flange 14. The flexible plastic member 16 also comprises a rim 20 surrounding the flange ring 18. The flexible plastic member 16 also comprises first and second loops 22, 24 extending radially from the rim 20. Each of the first and second loops 22, 24 comprises a raised fence 26 around an opening that forms a pocket 28. The body flange 14 also comprises an adhesive skin barrier member 30 located on an opposite second side of the body flange 14. The mounting assembly also comprises an ostomy pouch 32. The ostomy pouch 32 comprises a proximal sheet 34 having an aperture 36. The ostomy pouch 32 also comprises a distal sheet 38 sealed to the proximal sheet 34 at their respective peripheries to form the ostomy pouch 32. The ostomy pouch 32 also comprises a pouch ring 40 attached to the proximal sheet 34, surrounding the aperture 36 of the proximal sheet 34. The pouch ring 40 comprises an adhesive coating 42 on the pouch ring 40. The pouch ring 40 also comprises third and fourth loops 44, 46 extending radially from the pouch ring 40. The body flange 14 and ostomy pouch 32 are configured for the third and fourth loops 44, 46 to engage within the pocket 28 of the first and second loops 22, 24, respectively, the pouch ring 40 to fit around the flange ring 18, and the rim 20 of the flexible plastic member 16 to contact the adhesive coating 42 on the pouch ring 40, for assembly of the ostomy appliance 12. The adhesive skin barrier member 30 has a multi-petaled outer perimeter 48 that has a shape corresponding to 2 to 8 petals 50 extending radially from the adhesive skin barrier member 30, distributed uniformly around the adhesive skin barrier member 30, and separated by notches 52 that expand radially from the adhesive skin barrier member 30.

The body flange 14 and the ostomy pouch 32 are in assembled engagement based on the third and fourth loops 44, 46 engaging within the pocket 28 of the first and second loops 22, 24, respectively, the pouch ring 40 fitting around the flange ring 18, and the rim 20 of the flexible plastic member 16 contacting the adhesive coating 42 on the pouch ring 40.

In accordance with some examples, the flexible plastic member 16 further comprises a central dome 56.

Also in accordance with some examples, the body flange 14 further comprises (a) a first double-sided adhesive substrate member 58 adhered to the flexible plastic member 16 opposite the flange ring 18, and having a size smaller than the multi-petaled outer perimeter 48 of the adhesive skin barrier member 30, and (b) a second double-sided adhesive substrate member 60 adhered to the first double-sided adhesive substrate member 58 and the adhesive skin barrier member 30 and having a multi-petaled outer perimeter 49 that substantially corresponds in size and shape to the multi-petaled outer perimeter 48 of the adhesive skin barrier member 30.

Also in accordance with some examples, the 2 to 8 petals 50 each have a width that first increases, then decreases, radially outwardly from the adhesive skin barrier member 30.

Also in accordance with some examples, the adhesive skin barrier member 30 has a maximum radius 66, and at least 50% of the multi-petaled outer perimeter 48 of the adhesive skin barrier member 30 extends to the maximum radius 66 of the adhesive skin barrier member 30.

Also in accordance with some examples, the shape of the multi-petaled outer perimeter 48 of the adhesive skin barrier member 30 corresponds to 3 to 6 petals 50.

Also in accordance with some examples, the rim 20 of the flexible plastic member 16 is substantially annular.

Also in accordance with some examples, the first and second loops 22, 24 are diametrically opposed, and the third and fourth loops 44, 46 are diametrically opposed.

Also in accordance with some examples, the adhesive skin barrier member 30 comprises an elastomer hydrocolloid mixture.

Also in accordance with some examples, the mounting assembly further comprises a first removable protective film 68 covering the adhesive skin barrier member 30, and a second removable protective film 70 covering the adhesive coating 42 on the pouch ring 40.

The ostomy appliance 12 can be disassembled, to separate the ostomy pouch 32 from the body flange 14, e.g. to replace the ostomy pouch 32 as used with an ostomy pouch 32 that has not yet been used, as described above. Thus, in some examples, the rim 20 of the flexible plastic member 16 further comprises a tab 80 extending axially therefrom, and the pouch ring 40 also further comprises a tab 82 extending axially therefrom, and in accordance with these examples, the tab 80 of the flexible plastic member 16 and the tab 82 of the pouch ring 40 can be used for disassembly of the ostomy appliance 12 as described above.

Also disclosed is a method of adhering an ostomy appliance 12 to an ostomate at a peristomal skin surface of the ostomate. In accordance with the method, the ostomy appliance 12 comprises a mounting assembly.

The mounting assembly is as described above. Accordingly, the mounting assembly comprises a body flange 14. The body flange 14 comprises a flexible plastic member 16 located on a first side of the body flange 14. The flexible plastic member 16 comprises a flange ring 18 projecting axially from the body flange 14. The flexible plastic member 16 also comprises a rim 20 surrounding the flange ring 18. The flexible plastic member 16 also comprises first and second loops 22, 24 extending radially from the rim 20. Each of the first and second loops 22, 24 comprises a raised fence 26 around an opening that forms a pocket 28. The body flange 14 also comprises an adhesive skin barrier member 30 located on an opposite second side of the body flange 14. The mounting assembly also comprises an ostomy pouch 32. The ostomy pouch 32 comprises a proximal sheet 34 having an aperture 36. The ostomy pouch 32 also comprises a distal sheet 38 sealed to the proximal sheet 34 at their respective peripheries to form the ostomy pouch 32. The ostomy pouch 32 also comprises a pouch ring 40 attached to the proximal sheet 34, surrounding the aperture 36 of the proximal sheet 34. The pouch ring 40 comprises an adhesive coating 42 on the pouch ring 40. The pouch ring 40 also comprises third and fourth loops 44, 46 extending radially from the pouch ring 40. The body flange 14 and ostomy pouch 32 are configured for the third and fourth loops 44, 46 to engage within the pocket 28 of the first and second loops 22, 24, respectively, the pouch ring 40 to fit around the flange ring 18, and the rim 20 of the flexible plastic member 16 to contact the adhesive coating 42 on the pouch ring 40, for assembly of the ostomy appliance. The adhesive skin barrier member 30 has a multi-petaled outer perimeter 48 that has a shape corresponding to 2 to 8 petals 50 extending radially from the adhesive skin barrier member 30, distributed uniformly around the adhesive skin barrier member 30, and separated by notches 52 that expand radially from the adhesive skin barrier member 30.

The flexible plastic member 16 and the adhesive skin barrier member 30 each have a stoma inlet portal 74, 76, respectively, centrally positioned and extending therethrough.

The method comprises a step of (1) placing the adhesive skin barrier member 30 at the peristomal region of the ostomate, such that the stoma inlet portals 74, 76 of the flexible plastic member 16 and the adhesive skin barrier member 30 are aligned with a stoma of the ostomate. The method also comprises a step of (2) engaging the third loop 44 with the pocket 28 of the first loop 22. The method also comprises a step of (3) fitting the pouch ring 40 around the flange ring 18. The method also comprises a step of (4) engaging the fourth loop 46 with the pocket 28 of the second loop 24. The method also comprises a step of (5) contacting the rim 20 of the flexible plastic member 16 to the adhesive coating 42 on the pouch ring 40. In accordance with the method, the ostomy appliance 12 is thereby adhered to the ostomate at the peristomal skin surface of the ostomate. Although the steps are presented in order of steps (1) to step (5), the steps may be carried out in other orders as appropriate, e.g. in an order of steps (1), (2), (4), (3), and (5), among others orders. Moreover, certain steps may be carried out simultaneously as appropriate, e.g. steps (2) and (4) may be carried out simultaneously.

In accordance with some examples, the mounting assembly further comprises a first removable protective film 68 covering the adhesive skin barrier member 30, and a second removable protective film 70 covering the adhesive coating 42 on the pouch ring 40. In accordance with these examples, the method further comprises a step of removing the first removable protective film 68 from the adhesive skin barrier member 30 prior to step (1), and a step of removing the second removable protective film 70 from the adhesive coating 42 on the pouch ring 40 prior to steps (2) to (5).

In accordance with some examples, the ostomy appliance 12 adheres to the ostomate at the peristomal skin surface of the ostomate with a smooth fit. For example, the ostomy appliance 12 can adhere to the ostomate at the peristomal skin surface of the ostomate with a smooth fit such that the multi-petaled body flange 14 is adapted to the peristomal skin surface of the ostomate, without undesirable bunching upon application. Also for example, the ostomy appliance 12 can adhere to the ostomate at the peristomal skin surface of the ostomate with a smooth fit across a range of peristomal skin surface contours of ostomates, e.g. for ostomates with peristomal skin surfaces that are flat, curved, bulging, and/or irregular. As the pouch fills with body waste, the adhesive skin barrier member 30 will remain secure and stay attached at the peristomal skin surface of the ostomate, and not peel away.

Also in accordance with some examples, the ostomy appliance 12 adheres to the ostomate at the peristomal skin surface of the ostomate without application of adhesive tape to the ostomy appliance 12 or to the ostomate. For example, the ostomy appliance 12 can adhere to the ostomate at the peristomal skin surface of the ostomate without application of adhesive tape to the ostomy appliance 12 or to the ostomate such that no adhesive tape needs to be applied to smooth, press, or adhere the body flange 14 to the skin at and adjacent the peristomal skin surface of the ostomate. Also for example, the ostomy appliance 12 can adhere to the ostomate at the peristomal skin surface of the ostomate without application of adhesive tape to the ostomy appliance 12 or to the ostomate across a range of peristomal skin surface contours of ostomates, e.g. for ostomates with peristomal skin surfaces that are flat, curved, bulging, and/or irregular. Again, as the pouch fills with body waste, the adhesive skin barrier member 30 will remain secure and stay attached at the peristomal skin surface of the ostomate, and not peel away.

In accordance with some examples, the flexible plastic member 16 further comprises a central dome 56.

Also in accordance with some examples, the body flange 14 further comprises (a) a first double-sided adhesive substrate member 58 adhered to the flexible plastic member 16 opposite the flange ring 18, and having a size smaller than the multi-petaled outer perimeter 48 of the adhesive skin barrier member 30, and (b) a second double-sided adhesive substrate member 60 adhered to the first double-sided adhesive substrate member 58 and the adhesive skin barrier member 30 and having a multi-petaled outer perimeter 49 that substantially corresponds in size and shape to the multi-petaled outer perimeter 48 of the adhesive skin barrier member 30.

Also in accordance with some examples, the 2 to 8 petals 50 each have a width that first increases, then decreases, radially outwardly from the adhesive skin barrier member 30.

Also in accordance with some examples, the adhesive skin barrier member 30 has a maximum radius 66, and at least 50% of the multi-petaled outer perimeter 48 of the adhesive skin barrier member 30 extends to the maximum radius 66 of the adhesive skin barrier member 30.

Also in accordance with some examples, the shape of the multi-petaled outer perimeter 48 of the adhesive skin barrier member 30 corresponds to 3 to 6 petals 50.

Also in accordance with some examples, the rim 20 of the flexible plastic member 16 is substantially annular.

Also in accordance with some examples, the first and second loops 22, 24 are diametrically opposed, and the third and fourth loops 44, 46 are diametrically opposed.

Also in accordance with some examples, the adhesive skin barrier member 30 comprises an elastomer hydrocolloid mixture.

Also in accordance with some examples, the mounting assembly further comprises a first removable protective film 68 covering the adhesive skin barrier member 30, and a second removable protective film 70 covering the adhesive coating 42 on the pouch ring 40.

Also in accordance with the method, the ostomy appliance 12 can be disassembled, to separate the ostomy pouch 32 from the body flange 14, e.g. to replace the ostomy pouch 32 as used with an ostomy pouch 32 that has not yet been used, as described above. Thus, in some examples, the rim 20 of the flexible plastic member 16 further comprises a tab 80 extending axially therefrom, and the pouch ring 40 also further comprises a tab 82 extending axially therefrom, and in accordance with these examples, the tab 80 of the flexible plastic member 16 and the tab 82 of the pouch ring 40 can be used for disassembly of the ostomy appliance 12 as described above.

Also disclosed is another method of adhering an ostomy appliance 12 to an ostomate at a peristomal skin surface of the ostomate. In accordance with the method, the ostomy appliance 12 comprises a mounting assembly.

The mounting assembly is as described above. Accordingly, the mounting assembly comprises a body flange 14. The body flange 14 comprises a flexible plastic member 16 located on a first side of the body flange 14. The flexible plastic member 16 comprises a flange ring 18 projecting axially from the body flange 14. The flexible plastic member 16 also comprises a rim 20 surrounding the flange ring 18. The flexible plastic member 16 also comprises first and second loops 22, 24 extending radially from the rim 20. Each of the first and second loops 22, 24 comprises a raised fence 26 around an opening that forms a pocket 28. The body flange 14 also comprises an adhesive skin barrier member 30 located on an opposite second side of the body flange 14. The mounting assembly also comprises an ostomy pouch 32. The ostomy pouch 32 comprises a proximal sheet 34 having an aperture 36. The ostomy pouch 32 also comprises a distal sheet 38 sealed to the proximal sheet 34 at their respective peripheries to form the ostomy pouch 32. The ostomy pouch 32 also comprises a pouch ring 40 attached to the proximal sheet 34, surrounding the aperture 36 of the proximal sheet 34. The pouch ring 40 comprises an adhesive coating 42 on the pouch ring 40. The pouch ring 40 also comprises third and fourth loops 44, 46 extending radially from the pouch ring 40. The body flange 14 and ostomy pouch 32 are configured for the third and fourth loops 44, 46 to engage within the pocket 28 of the first and second loops 22, 24, respectively, the pouch ring 40 to fit around the flange ring 18, and the rim 20 of the flexible plastic member 16 to contact the adhesive coating 42 on the pouch ring 40, for assembly of the ostomy appliance 12. The adhesive skin barrier member 30 has a multi-petaled outer perimeter 48 that has a shape corresponding to 2 to 8 petals 50 extending radially from the adhesive skin barrier member 30, distributed uniformly around the adhesive skin barrier member 30, and separated by notches 52 that expand radially from the adhesive skin barrier member 30.

The method comprises a step of (0) cutting a stoma inlet portal 76 through at least the adhesive skin barrier member 30, such that the flexible plastic member 16 and the adhesive skin barrier member 30 each have a stoma inlet portal 74, 76, respectively centrally positioned and extending therethrough. The method also comprises a step of (1) placing the adhesive skin barrier member 30 at the peristomal region of the ostomate, such that the stoma inlet portals 74, 76 of the flexible plastic member 16 and the adhesive skin barrier member 30 are aligned with a stoma of the ostomate. The method also comprises a step of (2) engaging the third loop 44 with the pocket 28 of the first loop 22. The method also comprises a step of (3) fitting the pouch ring 40 around the flange ring 18. The method also comprises a step of (4) engaging the fourth loop 46 with the pocket 28 of the second loop 24. The method also comprises a step of (5) contacting the rim 20 of the flexible plastic member 16 to the adhesive coating 42 on the pouch ring 40. In accordance with the method, the ostomy appliance 12 is thereby adhered to the ostomate at the peristomal skin surface of the ostomate.

In accordance with some examples, the mounting assembly further comprises a first removable protective film 68 covering the adhesive skin barrier member 30, and a second removable protective film 70 covering the adhesive coating 42 on the pouch ring 40. In accordance with these examples, the method further comprises a step of removing the first removable protective film 68 from the adhesive skin barrier member 30 prior to steps (0) and (1), and a step of removing the second removable protective film 70 from the adhesive coating 42 on the pouch ring 40 prior to steps (2) to (5).

Also in accordance with some examples, the ostomy appliance 12 adheres to the ostomate at the peristomal skin surface of the ostomate with a smooth fit.

Also in accordance with some examples, the ostomy appliance 12 adheres to the ostomate at the peristomal skin surface of the ostomate without application of adhesive tape to the ostomy appliance 12 or to the ostomate.

In accordance with some examples, the flexible plastic member 16 further comprises a central dome 56.

Also in accordance with some examples, the body flange 14 further comprises (a) a first double-sided adhesive substrate member 58 adhered to the flexible plastic member 16 opposite the flange ring 18, and having a size smaller than the multi-petaled outer perimeter 48 of the adhesive skin barrier member 30, and (b) a second double-sided adhesive substrate member 60 adhered to the first double-sided adhesive substrate member 58 and the adhesive skin barrier member 30 and having a multi-petaled outer perimeter 49 that substantially corresponds in size and shape to the multi-petaled outer perimeter 48 of the adhesive skin barrier member 30.

Also in accordance with some examples, the 2 to 8 petals 50 each have a width that first increases, then decreases, radially outwardly from the adhesive skin barrier member 30.

Also in accordance with some examples, the adhesive skin barrier member 30 has a maximum radius 66, and at least 50% of the multi-petaled outer perimeter 48 of the adhesive skin barrier member 30 extends to the maximum radius 66 of the adhesive skin barrier member 30.

Also in accordance with some examples, the shape of the multi-petaled outer perimeter 48 of the adhesive skin barrier member 30 corresponds to 3 to 6 petals 50.

Also in accordance with some examples, the rim 20 of the flexible plastic member 16 is substantially annular.

Also in accordance with some examples, the first and second loops 22, 24 are diametrically opposed, and the third and fourth loops 44, 46 are diametrically opposed.

Also in accordance with some examples, the adhesive skin barrier member 30 comprises an elastomer hydrocolloid mixture.

Also in accordance with some examples, the mounting assembly further comprises a first removable protective film 68 covering the adhesive skin barrier member 30, and a second removable protective film 70 covering the adhesive coating 42 on the pouch ring 40.

Also in accordance with the method, the ostomy appliance 12 can be disassembled, to separate the ostomy pouch 32 from the body flange 14, e.g. to replace the ostomy pouch 32 as used with an ostomy pouch 32 that has not yet been used, as described above. Thus, in some examples, the rim 20 of the flexible plastic member 16 further comprises a tab 80 extending axially therefrom, and the pouch ring 40 also further comprises a tab 82 extending axially therefrom, and in accordance with these examples, the tab 80 of the flexible plastic member 16 and the tab 82 of the pouch ring 40 can be used for disassembly of the ostomy appliance 12 as described above.

EXAMPLES

Comparisons of surface adhesion by multi-petaled body flanges for a mounting assembly for an ostomy appliance versus circular (i.e. non-multi-petaled) body flanges for a mounting assembly for an ostomy appliance were carried out. The comparisons involved the following steps. First, a multi-petaled body flange and a circular body flange were applied to a curved surface of an object, such that most of each body flange was pressed by hand to the curved surface. Next, it was observed whether the application of each body flange had been accomplished with a smooth fit or whether undesirable bunching had occurred. Then the object was kept at approximately 24° C. for approximately 24 hours. Finally, it was observed whether peeling of either of the body flanges from the curved surface of the object had occurred where each body flange had been pressed by hand to the curved surface.

Two objects were used, a ball and a vase. The ball had a curved surface corresponding to a round surface. The vase had a curved surface corresponding to a convex surface. The curved surfaces were analogous to peristomal skin surfaces of ostomates, such as, for example, a curved abdominal surface associated with an ostomate who is overweight and, also for example, a curved abdominal surface associated with an ostomate who is bending at the waist. The multi-petaled body flanges and the circular body flanges both included the same adhesive, corresponding to an elastomer hydrocolloid mixture that is used commercially on body flanges of ostomy appliances. The adhesive is not specific to skin and would be expected to accomplish adhesion similarly for the ball and the vase as for skin.

For these comparisons, surface adhesion by the multi-petaled body flanges and the circular body flanges was tested without ostomy pouches attached to the body flanges. This was because the comparisons were focused on adhesion of the body flanges to the curved surfaces of the ball and the vase, and attachment of ostomy pouches to the body flanges would have obscured views of the body flanges as adhered to the curved surfaces.

Results of four comparisons are shown in FIG. 8, FIG. 9, FIG. 10, and FIG. 11.

In a first comparison, following application of a multi-petaled body flange and a circular body flange to the curved surface of the ball, such that most of each body flange was pressed by hand to the curved surface, it was observed that application of the multi-petaled body flange had been accomplished with a smooth fit (FIG. 8A, left side, top half), whereas undesirable bunching had occurred upon application of the circular body flange (FIG. 8A, right side, top half). Also, after the ball had been kept at approximately 24° C. for approximately 24 hours, it was observed that no peeling of the multi-petaled body flange from the ball had occurred where the multi-petaled body flange had been pressed by hand to the curved surface (FIG. 8B, right side, top half), whereas peeling of the circular body flange from the ball had occurred where the circular body flange had been pressed by hand to the curved surface (FIG. 8B, left side, top half).

Similarly, in a second comparison, following application of a multi-petaled body flange and a circular body flange to the curved surface of the vase, such that most of each body flange was pressed by hand to the curved surface, it was observed that application of the multi-petaled body flange had been accomplished with a smooth fit (FIG. 9A, left side, top half), whereas undesirable bunching had occurred upon application of the circular body flange (FIG. 9A, right side, top half). Also, after the vase had been kept at approximately 24° C. for approximately 24 hours, it was observed that no peeling of the multi-petaled body flange from the vase had occurred where the multi-petaled body flange had been pressed by hand to the curved surface (FIG. 9B, left side, top half), whereas peeling of the circular body flange from the vase had occurred where the circular body flange had been pressed by hand to the curved surface (FIG. 9B, right side, top half).

Similar results were obtained in a third comparison as in the first comparison. It was observed that application of the multi-petaled body flange had been accomplished with a smooth fit (FIG. 10A, right side, top half), whereas undesirable bunching had occurred upon application of the circular body flange (FIG. 10A, left side, top half). Also, after approximately 24 hours, it was observed that no peeling of the multi-petaled body flange from the ball had occurred where the multi-petaled body flange had been pressed by hand to the curved surface (FIG. 10B, right side, bottom half), whereas peeling of the circular body flange from the ball had occurred where the circular body flange had been pressed by hand to the curved surface (FIG. 10B, left side, top half).

Similar results also were obtained in a fourth comparison as in the second comparison. It was observed that application of the multi-petaled body flange had been accomplished with a smooth fit (FIG. 11A, left side, top half), whereas undesirable bunching had occurred upon application of the circular body flange (FIG. 11A, right side, top half). Also, after approximately 24 hours, it was observed that no peeling of the multi-petaled body flange from the vase had occurred where the multi-petaled body flange had been pressed by hand to the curved surface (FIG. 11B, left side, top half), whereas peeling of the circular body flange from the vase had occurred where the circular body flange had been pressed by hand to the curved surface (FIG. 11B, right side, top half).

The results demonstrate that a multi-petaled body flange of a mounting assembly for an ostomy appliance can adhere to curved surfaces analogous to peristomal skin surfaces of ostomates with a smooth fit, without undesirable bunching upon application and across a range of surface contours, consistent with an ostomy appliance comprising the multi-petaled body flange doing the same. The results also demonstrate that a multi-petaled body flange can adhere to curved surfaces analogous to peristomal skin surfaces of ostomates without application of adhesive tape to the multi-petaled body flange or the curved surfaces, such that no adhesive tape needs to be applied to smooth, press, or adhere the body flange to the surface and across a range of surface contours, also consistent with an ostomy appliance comprising the multi-petaled body flange doing the same. Based on these results, it is believed that the multi-petaled body flange can provide longer wear times relative to the circular body flange, e.g. wear times of 3 to 5 days versus wear times of several hours to half of a day, particularly as a corresponding ostomy pouch fills with body waste and the weight of the ostomy pouch thus increases.

INDUSTRIAL APPLICABILITY

The mounting assembly for an ostomy appliance disclosed herein is useful for collection of waste from surgically diverted organs of ostomates.

The invention claimed is:

1. A mounting assembly for an ostomy appliance, comprising:
   (a) a body flange comprising:
   (i) a flexible plastic member located on a first side of the body flange, the flexible plastic member comprising a flange ring projecting axially from the body flange, a rim surrounding the flange ring, and first and second loops extending radially from the rim, each of the first and second loops comprising a raised fence around an opening that forms a pocket, and
   (ii) an adhesive skin barrier member located on an opposite second side of the body flange, and
   (b) an ostomy pouch comprising:
   (i) a proximal sheet having an aperture,
   (ii) a distal sheet sealed to the proximal sheet at their respective peripheries to form the ostomy pouch, and
   (iii) a pouch ring attached to the proximal sheet, surrounding the aperture of the proximal sheet, the pouch ring comprising an adhesive coating on the pouch ring and third and fourth loops extending radially from the pouch ring,
   wherein the body flange and ostomy pouch are configured for the third and fourth loops to engage within the pocket of the first and second loops, respectively, the pouch ring to fit around the flange ring, and the rim of the flexible plastic member to contact the adhesive coating on the pouch ring, for assembly of the ostomy appliance;
   the adhesive skin barrier member has a multi-petaled outer perimeter that has a shape corresponding to 2 to 8 petals extending radially from the adhesive skin barrier member, distributed uniformly around the adhesive skin barrier member, and separated by notches that expand radially from the adhesive skin barrier member, wherein each of the 2 to 8 petals intersects angularly with each petal adjacent thereto, thereby defining the notches;
   and
   the 2 to 8 petals each have a width that first increases, then decreases, radially outwardly from the adhesive skin barrier member.

2. The mounting assembly of claim 1, wherein the flexible plastic member further comprises a central dome.

3. The mounting assembly of claim 1, wherein the body flange further comprises:
   (a) a first double-sided adhesive substrate member adhered to the flexible plastic member opposite the flange ring, and having a size smaller than the multi-petaled outer perimeter of the adhesive skin barrier member, and
   (b) a second double-sided adhesive substrate member adhered to the first double-sided adhesive substrate member and the adhesive skin barrier member and having a multi-petaled outer perimeter that substantially corresponds in size and shape to the multi-petaled outer perimeter of the adhesive skin barrier member.

4. The mounting assembly of claim 1, wherein the adhesive skin barrier member has a maximum radius, and at least 50% of the multi-petaled outer perimeter of the adhesive skin barrier member extends to the maximum radius of the adhesive skin barrier member.

5. The mounting assembly of claim 1, wherein the shape of the multi-petaled outer perimeter of the adhesive skin barrier member corresponds to 3 to 6 petals.

6. The mounting assembly of claim 1, wherein the rim of the flexible plastic member is substantially annular.

7. The mounting assembly of claim 1, wherein the first and second loops are diametrically opposed, and the third and fourth loops are diametrically opposed.

8. The mounting assembly of claim 1, wherein the adhesive skin barrier member comprises an elastomer hydrocolloid mixture.

9. The mounting assembly of claim 1, further comprising a first removable protective film covering the adhesive skin barrier member, and a second removable protective film covering the adhesive coating on the pouch ring.

10. The mounting assembly of claim 1, wherein the flexible plastic member and the adhesive skin barrier member each have a stoma inlet portal, centrally positioned and extending therethrough.

11. An ostomy appliance comprising the mounting assembly of claim 1, wherein the body flange and the ostomy pouch are in assembled engagement based on the third and fourth loops engaging within the pocket of the first and second loops, respectively, the pouch ring fitting around the flange ring, and the rim of the flexible plastic member contacting the adhesive coating on the pouch ring.

12. The mounting assembly of claim 1, wherein the width of each of the 2 to 8 petals is a width measured as an arcuate length with respect to a center of the adhesive skin barrier member.

* * * * *